United States Patent [19]

Nishimura et al.

[11] Patent Number: 4,907,457
[45] Date of Patent: Mar. 13, 1990

[54] METHOD OF EVALUATING RESIDUAL LIFE OF HEAT-RESISTANT STEEL

[75] Inventors: Nobuhiko Nishimura; Fujimitsu Masuyama, both of Nagasaki; Tetsuro Sada, Tokyo, all of Japan

[73] Assignee: Mitsubishi Jukogyo Kabushiki Kaisha, Tokyo, Japan

[21] Appl. No.: 224,002

[22] Filed: Jul. 25, 1988

[30] Foreign Application Priority Data

Jul. 27, 1987 [JP] Japan .................. 62-185542
Oct. 9, 1987 [JP] Japan .................. 62-254929

[51] Int. Cl.$^4$ .......................................... G01N 21/00
[52] U.S. Cl. .................................................. 73/787
[58] Field of Search .................. 73/787, 760; 364/508

[56] References Cited

U.S. PATENT DOCUMENTS 4,768,383 9/1988 Koyama et al. .................. 73/787

OTHER PUBLICATIONS

Maruyama, T. et al., Estimation of Creep ... Alloys, Zairyo, vol. 28, No. 308, pp. 26–32.

Primary Examiner—Jerry W. Myracle
Attorney, Agent, or Firm—Wenderoth, Lind & Ponack

[57] ABSTRACT

A method of evaluating residual life of a heat-resistant steel member after and during service at high temperature and stress makes use of a residual life evaluation diagram which is obtained beforehand on a plurality of samples of the heat-resistant steel and which represents the relationship between the life consumption and a parameter which indicates the life consumed. The parameter may be data concerning the density of an alloy element such as molybdenum and chromium, or the state of degradation in the metallurgical structure and/or state of precipitation of carbides.

4 Claims, 7 Drawing Sheets

3μm

CREEP RUPTURE LIFE CONSUMPTION FACTOR (%)

3μm

METHOD OF EVALUATING RESIDUAL LIFE OF HEAT-RESISTANT STEEL

BACKGROUND OF THE INVENTION

1. Field of the Invention

The present invention relates to a method of evaluating residual life of heat resistant steels which are used under stressed conditions at high temperatures.

2. Description of the Prior Art

For instance, superheater tubes of boilers in power stations exhibit deterioration of the material during long use becaue they are used under severe conditions at high temperatures and pressures. If the life of the material is completely consumed, accident such as rupture may occur. In order to avoid such accident, various methods have been known for evaluating residual life of heat-resistant steels such as a creep rupture test of the material, a method relying upon examination of change in the mechanical strength such as hardness or change in structure or a method which employs non-destructive examination for detecting any crack.

Destructive examination such as a creep rupture test, however, requires laborious works such as sampling by cutting of actually used parts and long-term examination which is to be conducted for a long time well exceeding several thousands of hours. Thus, it is impossible to evaluate residual life in a short time and in a non-destructive manner with such a method. The method relying upon detection of change in the mechanical properties such as hardness could not provide accurate information concerning the residual life over a long period from the beginning until the end of use partly because the change in the mechanical properties takes place mainly in the end portion of the life and partly because the changing characteristics vary largely. It has been also known that the change in the structure during long use is one of the most critical factors of the deterioration of the material. However, no effective method has been proposed for enabling quantitative analysis of the change in the structure of heat-resistant steels for the purpose of evaluation of residual life. Non-destructive examination for detecting cracks in heat-resistant steel used at high temperature and stress is very effective for the purpose of evaluation of residual life but this method cannot provide any information concerning the state of material before the crack is actually generated.

The present invention has been developed to fill the gap between the level of the conventional art and the actual demand, by providing a method which enables an accurate evaluation of residual life of heat-resistant steel from information concerning a change in the density etc. of alloy element in heat-resistant steel.

To this end, according to the present invention, there is provided a method of evaluating the residual life of heat-resistant steel used at high temperature and pressure, having the following features.

According to a first aspect, there is provided a method for evaluating residual life of a heat-resistant steel after a service at high levels of temperature and stress comprising: measuring the density of an alloy element in a tiny region of each of a multiplicity of measuring spots on the surface of the heat-resistant steel; and obtaining a prediction value of the residual life by locating the data concerning the measured values of density of the alloy element on a residual life evaluation reference diagram which has been beforehand obtained and which represents the relationship between the density of the alloy element and the life consumption as obtained through a non-destructive test or a stress analysis on the heat-resistant steel used under various conditions.

According to a second aspect of the invention, there is provided a method for evaluating the residual life of a heat-resistant steel after a service at high levels of temperature and stress, comprising: obtaining a replica from the surface of the heat-resistant steel; determining the state of deterioration of metallurgical structure of the heat-resistant steel and/or the state of precipitates from the replica; and obtaining a prediction value of the residual life by locating the data concerning the determined values the state of deterioration of metallurgical structure and/or the state of precipitates on a residual life evaluation reference diagram which has been beforehand obtained and which represents the relationship between the state of deterioration of metallurgical structure and/or the state of precipitates and the life consumption as obtained through a non-destructive test or a stress analysis on the heat-resistant steel used under various conditions.

The present inventors have found, through an intense study concerning heat-resistant steel used at high temperature and pressure, that a very close correlation exists between the residual life of heat-resistant steel and state of densities of alloy elements of the steel and state of degradation of metallurgical structure of the steel and/or state of precipitation.

The present invention is based upon such a discovery. According to the invention, densities of alloy elements in tiny areas on the surface of the heat-resistant steel used is measured at a multiplicity of points or, alternatively, the state of degradation of metallurgical structure and/or state of precipitation is determined from a replica extracted from the surface of the heat-resistant steel. At the same time, correlations between these factors and the life consumption rate are beforehand obtained through a destructive test or stress analysis and data thus obtained are stored in the form of a residual life evaluation reference diagram. The residual life of the heat-resistant steel, therefore, can be evaluated by making reference to such a diagram.

According to the present invention, therefore, it is possible to accurately evaluate in a short time without necessitating any destructive exmination. In addition, the method of the invention can provide information concerning the residual life of the heat-resistant steel over a long period of time from the beginning of the use until the end of the service.

BRIEF DESCRIPTION OF THE DRAWINGS

FIGS. 1 to 3 are illustrations of a first embodiment of the present invention in which:

FIG. 1 is a schematic illustration of Mo density distribution as obtained with a non-used ferrite heat-resistant steel and a ferrite heat-resistant steel after a long use;

FIG. 2 is a residual life evaluation reference diagram showing the correlations between the maximum area factor of the Mo density distribution and creep rupture life consumption in the ferrite heat-resistant steel; and FIG. 3 is an illustration of a residual life evaluation reference diagram illustrating the relationship between the half-value width of Mo density of ferrite stainless steel and the creep rupture life consumption.

FIGS. 4 to 7 are illustrations of a second embodiment of the present invention in which:

FIG. 4 is an illustration of definition of the area factor which is a concept introduced by the present invention;

FIG. 5 is an illustration of definition of the unit density section which also is a concept introduced by the present invention;

FIG. 6 (including parts 6a and 6b) is a schematic illustration of Cr and Mo density spectrum in a ferrite heat-resistant steel after operation through 140,000 hours as a heat- and pressure-resistant part of a boiler in a power station; and FIG. 7 (including parts 7a and 7b) is a schematic illustration of residual life reference diagram which shows the correlation between logarithmic attenuation factors of Cr and Mo density spectrums in heat-resistant steel used under various conditions and the life consumption factor as determined through a rupture test.

FIGS. 8 and 9 are illustrations of a third embodiment of the present invention in which:

FIG. 8 is a schematic illustration of analytical electron microscopic structure of a thin film specimen as obtained from a fine sample of $3\phi \times 1$ t mm as extracted from a ferrite heat- and pressure-resistant member of a boiler used in a power station; and FIG. 9 is a residual life evaluation reference diagram repesenting the correlation between creep rupture life consumption and molybdenum density in matrix phase.

FIGS. 10 and 11 are illustrations of a fourth embodiment of the present invention in which:

FIG. 10 is a schematic illustration of an electron-microscopic structure for measuring the spheroidizing factor of grain boundary carbides; and FIG. 11 is an illustration of residual life evaluation reference diagram showing the correlation between the spheroidizing factor of grain boundary carbides and creep rupture life consumption.

FIGS. 13 and 14 are illustrations of a sixth embodiment of the present invention in which:

FIG. 13 is a schematic illustration of transmission electronmicroscopic structure of a replica extracted from the surface of a temperature- and pressure-resistant part of a boiler used for a long time in a power station; and FIG. 14 is an illustration of a residual life evaluation diagram representing the correlation between the $M_6C$ carbide precipitation and life consumption in a ferrite heat-resistant steel.

DESCRIPTION OF THE PREFERRED EMBODIMENTS

A first embodiment of the present invention will be described hereinunder. The present inventors conducted an intense study on ferrite heat-resistant steel and austenite heat-resistant steel which have been used for long time at high temperatures. As a result of the study, the inventors have found that, in the case of the ferrite heat-resistant steels, the deterioration of the steel is closely related to nodulation of $Mo_2C$ carbides in ferrite grains and precipitation coarsening of $M_6C$ carbides in the grain boundary which are caused during long use of the steel.

The inventors also found, in the case of austenite heat-resistant steel, the deterioration is closely related to precipitation of delta (δ) phase to the grain boundaries and resultant formation of chromium-lacking layer. The inventors further found that these structural changes in the respective types of heat-resistant steel can be detected through detection of a change in the density of molybdenum and chromium which are alloy elements of these steels.

The first embodiment of the invention is based upon such discoveries. Thus, in the first embodiment of the present invention, the change in the state of distribution of element density in heat-resistant steel is quantitatively measured and the residual life of the heat-resistant steel is evaluated from the measured data with reference to a residual life evaluation reference diagram showing the relationship between the quantitative value of the density distribution and the life consumption rate, the diagram being obtained through actual measurement by a destructive examination or stress analysis.

As regards $2\frac{1}{4}$ Cr-1 Mo ferrite heat-resistant steel and other ferrite heat-resistant steel which have been used long as the material of superheater tubes and main steam pipes of a boiler in a power station densities of Mo, which is an alloy element of this type of heat-resistant steel, are measured and analyzed by an X-ray analyzer at a multiplicity of $1 \times 1$ mm spots (1000 pots$\times$1000 spots).

Figure 1:
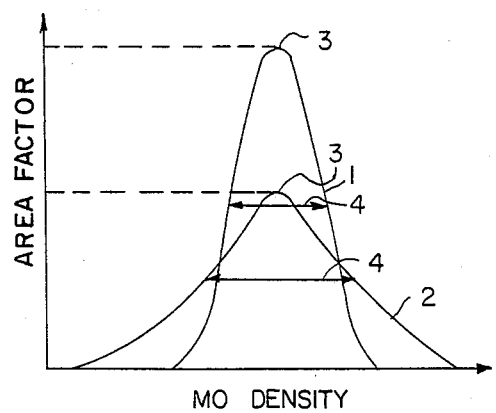
Figure 2:
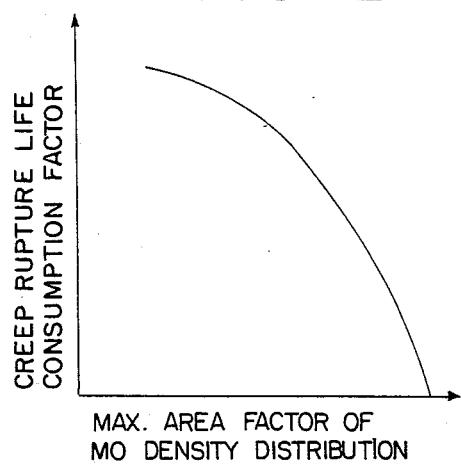
Figure 3:
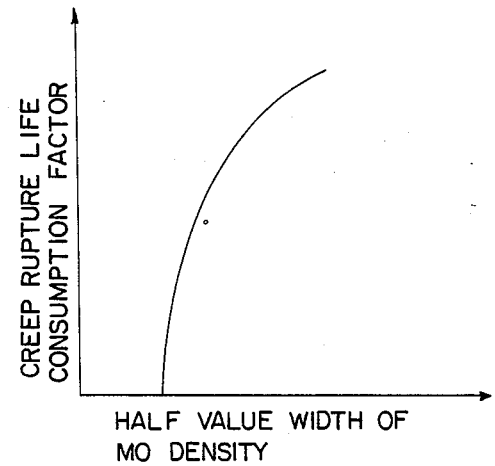
Figure 4:
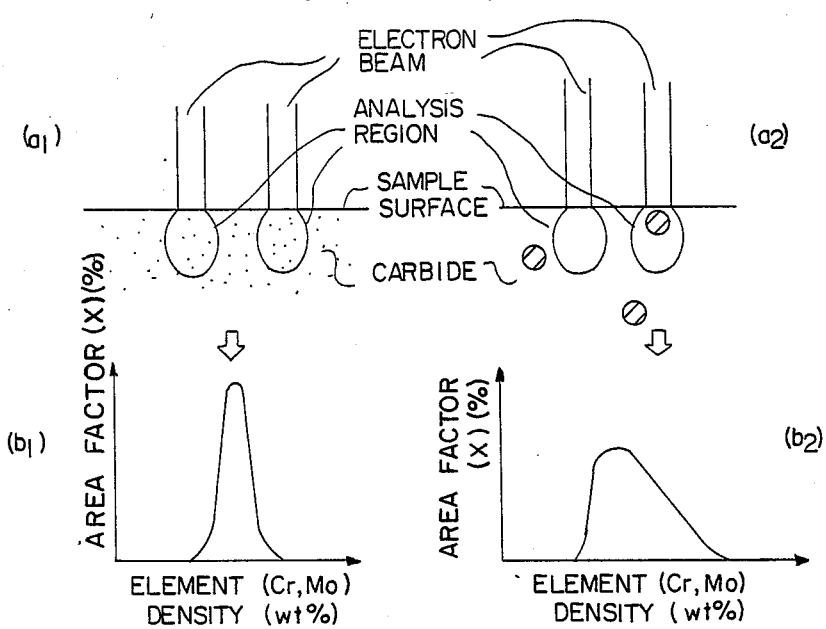

A gradation or scale was formed over the entire density range at a unit of 0.2%. The ratio of the number of the analysis spots ranging in each density region to the total number of the analysis spots was plotted along the density level. FIG. 1 show the Mo density distribution 1 in the non-used material and the Mo density distribution in the long-used material. The degree of unevenness of the Mo density caused during long used was evaluated in terms of the maximum value 3 of the area factor of Mo density distribution and the half-value width 4 of the distribution spectrum, and, for each of various steel materials, a residual life evaluation reference diagram was drawn which shows the correlation between the creep-rupture life consumption and the maximum value of the area factor or half value width of the distribution spectrum. FIG. 2 shows the residual life evaluation reference diagram plotted in accordance with the maximum area factor of Mo density distribution of $2\frac{1}{4}$Cr - 1Mo steel, while FIG. 3 shows the residual life evaluation reference diagram plotted on the basis of the half value width.

Then, the Mo density distribution was measured by the method described before in the surface region of superheater tubes used long in a boiler of a power station, and the creep rupture life consumption was predicted with reference to the residual life evaluation reference diagram by making use of the measured maximum area factor and the half value width. The value of the life consumption predicted on the basis of the maximum area factor was 53%, while the life consumption predicted on the basis of the half value width was 56%. On the other hand, the creep rupture life consumption of the superheater tube was measured by conducting a creep rupture test. The test showed a value of 51.4% which well confirmed with the values predicted by the method of the invention.

A residual life evaluation reference diagram was formed also for austenite steel on the basis of Cr density distribution, by a method substantially the same as that used for ferrite steel. The residual life was evaluated from the maximum area factor and the half value width of the Cr density distribution measured on the long-used sample materials. The result of the evaluation well conformed with the result of determination of life consumption through a creep rupture test.

A second embodiment of the present invention will be described hereinunder. The present inventors also found that the residual life of ferrite heat-resistant steel used at high temperature and a high stress level depends on the kind and shape of the carbides precipitated during the use of the steel. A test piece (a1) exhibits a uniform distribution of fine carbides. In this type of test piece, a substantially equal ratio of carbides is obtained over a plurality of analysis spot. Namely, the densities of elements constituting the carbides, which are Cr and Mo in the case of ferrite steels, are substantially constant regardless of the position of the analysis spot. Therefore, the density spectrum has a sharp peak in the region around mean density as will be seen from (b1).

In contrast, in a test piece (a2) in which carbides have been condensed and become coarse the ratio of carbides in the analysis region largely vary according to the position of the analysis spot, with the result that different analysis spots show different densities of carbide formers. In consequence, the spectrum shows only a low and wide peak as shown in (b2).

The inventors also have worked out a method which enables a quantitative detection of the change in the density distribution of chromium (Cr) and molybdenum (Mo) which are the carbide formers. More specifically, the inventors measured the densities of Cr and Mo in tiny regions at a multiplicity of analysis spots on the surface of a ferrite heat-resistant steel and, for each unit density section or region, the ratio of the analysis spot falling in each density region to the total number of the analysis spots was computed as an area factor. The value of area factors of the respective unit density regions were plotted along the density, for each of Cr and Mo. As a result, the inventors have found that the area factor attenuation ratio at the higher density side of the area factor of the density spectrum vary depending on factors such as the type of the precipitated carbides and state of distribution of such precipitated matters.

A description will be given below of the definition of the unit density section.

Figure 5:
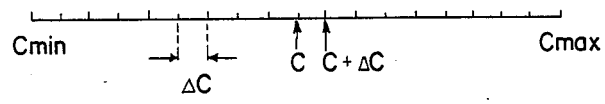

Referring to FIG. 5, the density range beween the minimum density (Cmin) and the maximum density (Cmax) for each of Cr and Mo as measured at the multiplicity of analysis spots is sectioned into n-pieces of density ($\Delta C$, e.g., 0.1 wt %) section. Each of such section will be referred to as unit density section (C to $C+\Delta C$).

$$\Delta C = (C_{max} - C_{min})/n \quad (n = \text{dividing number})$$

The area factor X(c) is defined as follows. Namely, the area factor X(c) is the ratio of the number of the analysis spot ($n_c$) falling in each unit density section (C to C+C) to the total numer (N) of the analysis spots. Thus, the area factor X(c) is given by the following formula.

$$X_c = \frac{n_c}{N} \times 100 \, (\%)$$

$$\text{where,} \quad \sum_{C=C_{min}, \Delta C}^{C_{max}} X(c) = 100$$

Figure 6A:
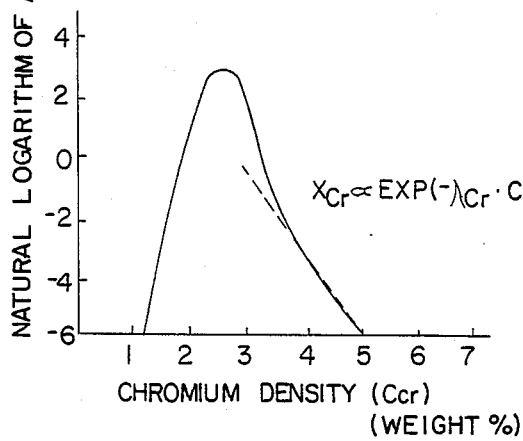
Figure 6B:
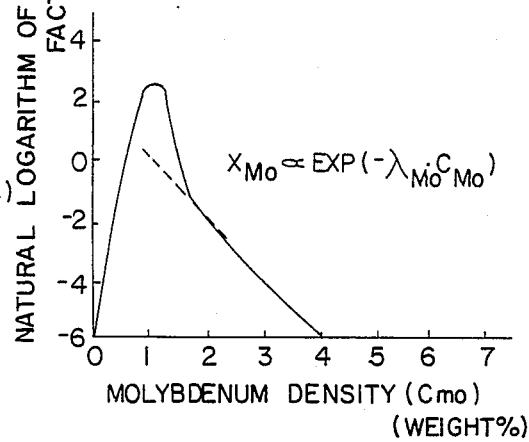

FIG. 6(a) shows CR density and FIG. 6(b) shows Mo density spectra of test pieces obtained by cutting, to the depth of several millimeters from the surface, a ferrite heat-resistant steel which has been used for 140,000 hours as the material of temperature- and pressure-resistant part of a boiler in a power station. In this Figure, the following symbols are used to mean the following factors.

$$X_{cr} = \frac{n(Cr)}{N} \times 100 \, (\%)$$

$$X_{Mo} = \frac{n(Mo)}{N} \times 100 \, (\%)$$

N: Total number of analysis spots
n(Cr): Number of analysis spots having Cr density ranging between $C_{cr}$ and $C_{CR} + \Delta C_{Cr}$
n(Mo): Number of analysis spots having Mo density ranging between $C_{Mo}$ and $C_{Mo} + \Delta C_{Mo}$ The area factor is plotted in terms of natural logarithm along the axis of ordinate. It will be seen that the natural logarithm of area factor linearly reduces with respect to the density particularly in higher density region, both in Cr density spectrum and Mo density spectrum. The gradient of such a linear change, i.e., the attenuation factors $\lambda_r$ and $\lambda_{Mo}$ were computed by least square method.

Figure 7A:
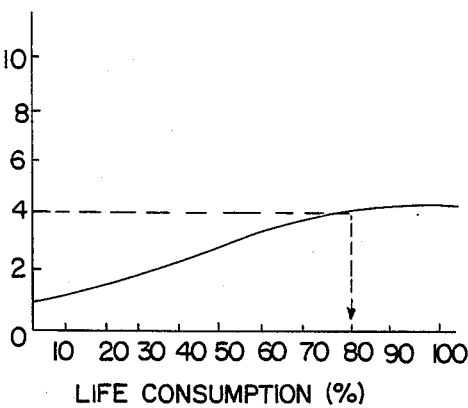
Figure 7B:
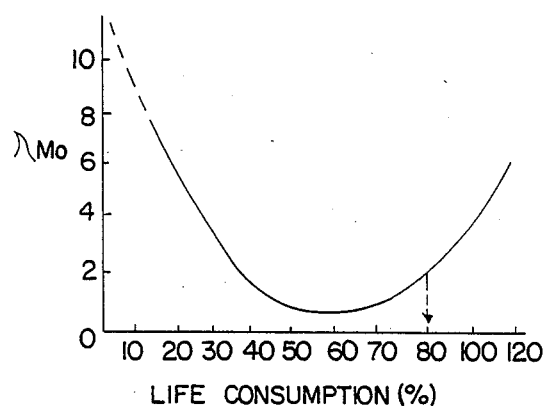

FIG. 7(a) and FIG. 7(b) respectively represent a residual life evaluation reference diagrams showing the relationship between the creep rupture life consumption and the Cr and Mo logarithmic attenuation factors as obtained with various materials after long use. The values of residual life as evaluated on the basis of the Cr density spectrum and the Mo density spectrum of the heat-resistant steel were 73% and 68%, respectively. On the other hand, residual life as measured by a creep rupture test of this steel was 65%. Thus, the offset of the residual life value determined by the method of the invention from the value determined through the creep rupture test was not greater than 10%. This means that the residual life evaluation method of the invention is effective.

A description will be given hereinunder of a third embodiment of the invention.

The inventors have conducted a fibrous analysis on a ferrite heat-resistant steel which has been used long as the material of a mechanical part used at high temperature. The inventors found that carbides constituted mainly by molybdenum coagulate and become coarse, while the molybdenum density in the matrix phase becomes small, in relation to the consumption of the life.

The third embodiment makes use of this fact. Namely, the molybdenum density of matrix phase in tiny sample extracted from a mechanical part which has been used long is measured, and is located on a life consumption evaluation diagram which has been formed beforehand to show the relationship between the molybdenum density and the life consumption, whereby the residual life is determined.

Figure 8:
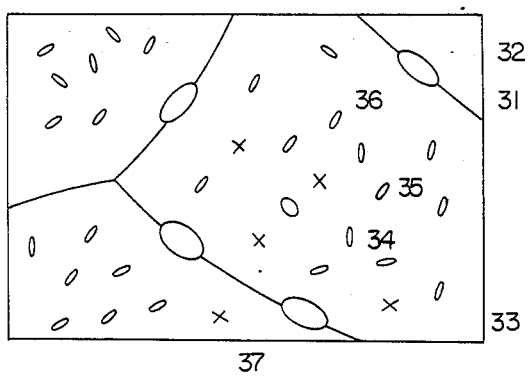

FIG. 8 is a schematic illustration of an analytical electronmicroscopic structure of a thin film specimen formed from a tiny sample of $3\phi \times 1$ t mm extracted from a ferrite heat- and pressure resistant steel member used in a boiler of a power station. From this Figure, it will be seen that many precipitation of coarse carbides 32 of $M_6C$ type mainly constituted by molybdenum, which did not exist before the use, are found on the grain boundaries. The molybdenum density therefore was measured at five points 33 to 37 in the matrix the result of which is shown in Table 1 from which it will be understood that the molybdenum density in the matrix phase has been decreased corresponding to the precipitation of $M_6C$ type coarse carbides.

TABLE 1

| Analysis spot (Reference Numeral in FIG. 1) | Mo Density (wt %) |
| --- | --- |
| 1 (33) | 0.68 |
| 2 (34) | 0.65 |
| 3 (35) | 0.66 |
| 4 (36) | 0.69 |
| 5 (37) | 0.67 |

Figure 9:
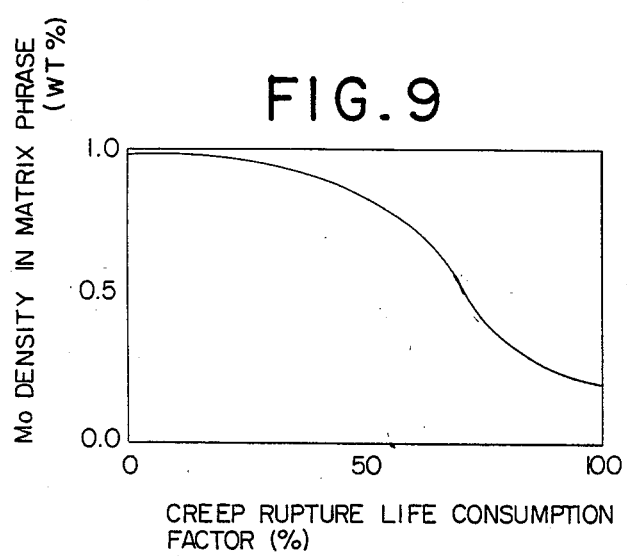

An examination was conducted in regard to the relationship between the creep rupture life consumption and the molybdenum density in the matrix phase for various materials which have been used long and artificial creep damaged materials. A good correlation was observed between the life consumption and the molybdenum density in the matrix phase, as will be seen from FIG. 9. Using the graph as the life evaluation reference diagram, the creep rupture life consumption of the ferrite heat-resistant steel was predicted to be 63% from the mean value of the density of molybdenum as an alloy element.

Then, the test piece was extracted from the same material and a creep rupture test was executed to determine the creep rupture life consumption. The life consumption determined by the creep rupture test was 58%.

From this fact, it is understood that the method of this embodiment which relies upon the density of molybdenum provides an evaluation result which is near to that obtained from the conventional evaluation method and, hence, sufficiently high reliability. Thus, the residual life can be determined with a high degree of reliability simply by measuring the molybdenum density.

A fourth embodiment of the invention will be described hereinunder.

The inventors have made an intense study on the ferrite heat-resistant steel after a long service, and found that this type of heat-resistant steel exhibits a tendency that the grain boundary precipitates are spheroidized when the steel is used for a long time at high temperature, and the degree of spheroidization depends on the levels of the temperature and stress during the use. As an index of degree of spheroidization in the ferrite heat-resistant steel after a long use at high temperature, a concept of spheroidizing factor was introduced as a ratio between the minimum value and the maximum value of the diameter of the sphere of the precipitated carbides. Thus, the spheroidization factor is given by the following formula.

$$\text{Spheroidizing factor} = \frac{\text{minimum dia. of carbides at grain boundary}}{\text{maximum dia. of carbides at grain boundary}}$$

The inventors have found that this novel concept of spheroidizing factor has a good correlation to the life consumption based upon stress analysis so that the residual life can be easily and accurately evaluated by measuring the spheroidizing factor.

In the fourth embodiment, therefore, the residual life of ferrite heat-resistant steel after a long use at high temperature can be evaluated by measuring spheroidizing factor of carbides precipitated in the grain boudaries and locating the thus measured spheroidizing factor on a residual life evaluation reference diagram which shows the relationship between the spheroidizing factor mentioned above and the life consumption, the relationship being beforehand obtained through a destructive test or through stress analyses.

$1\frac{1}{4}$Cr - 1Mo ferrite heat-resistant steel and other ferrite resistant steels after a long service as the material of temperature- and pressure- resistant member of boilers were observed through an electron microscope.

Figure 10:
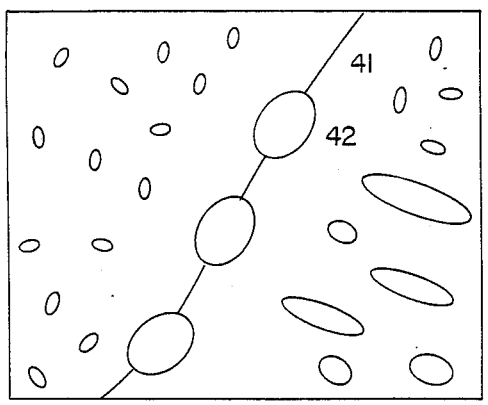

FIG. 10 is a schematic illustration of the structure of these steels observed through the electron microscope. The maximum value $1_a$ and the minimum value $1_b$ of grain boundary carbides 42 on the grain boundary 41 were measured for each of these materials and the spheroidizing factor was computed as the ratio $1_b/1_a$.

Figure 11:
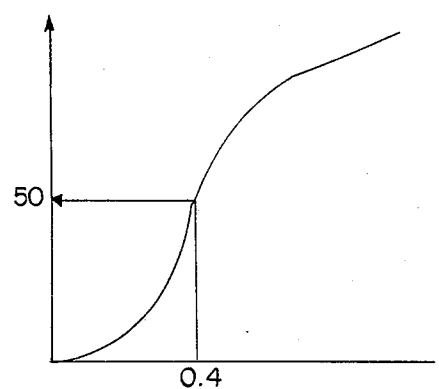

Then, a creep rupture test was conducted and the life consumption was computed as a ratio of the creep rupture time between the used material and non-used material, whereby a residual life evaluation reference diagram as shown in FIG. 11 was obtained to show the relationship between the spheroidizing factor and the creep rupture life consumption.

Subsequently, replica samples were obtained from the surface of superheater tubes of a power station boiler after a long service, and the spheroidizing factors of the grain boundary carbides were measured in accordance with the method described before. By locating this value of the spheroidizing factor on the curve of the residual life evaluation reference diagram, the creep rupture life consumption was predicted to be 50%.

A creep rupture test was carried out on the same superheater tube materials and non-used materials at a temperature 600° C. and stress levels 10 kg/mm². The rupture time was 1110 hours in case of the used material and 2140 hours in case of the non-used material. Thus, the life consumption of the used material is 51.4%. This value well approaches the value predicted by the method of this embodiment.

Thus, the described embodiment makes it possible to determine the residual life of ferrite heat-resistant steel after a long use at high temperature.

A description will be given hereinunder of a fifth embodiment of the present invention.

In the method of evaluation of residual life of heat-resistant steel according to this embodiment, replica and extract replica are obtained from the surface of the heat-resistant steel and correlation between the defect distribution in the heat-resistant steel and the residual life is determined in accordance with these replicas. In addition, the state of deterioration of metallurgical structure of the heat-resistant steel is determined on the base of the replica and distribution of precipitates is determined in accordance with the extract replica. Then, correlations between the results and the life section of the heat-resistant steel are determined. Thus, this embodiment makes use of the correlation between the defect distribution and the residual life and the correlation between the deterioration state and precipitate distribution and the life section. Using these correlations, it is possible to evaluate the residual life of heat-resistant steel in a non-destructive manner and in a short time from the beginning till the end of the service period.

Figure 12:
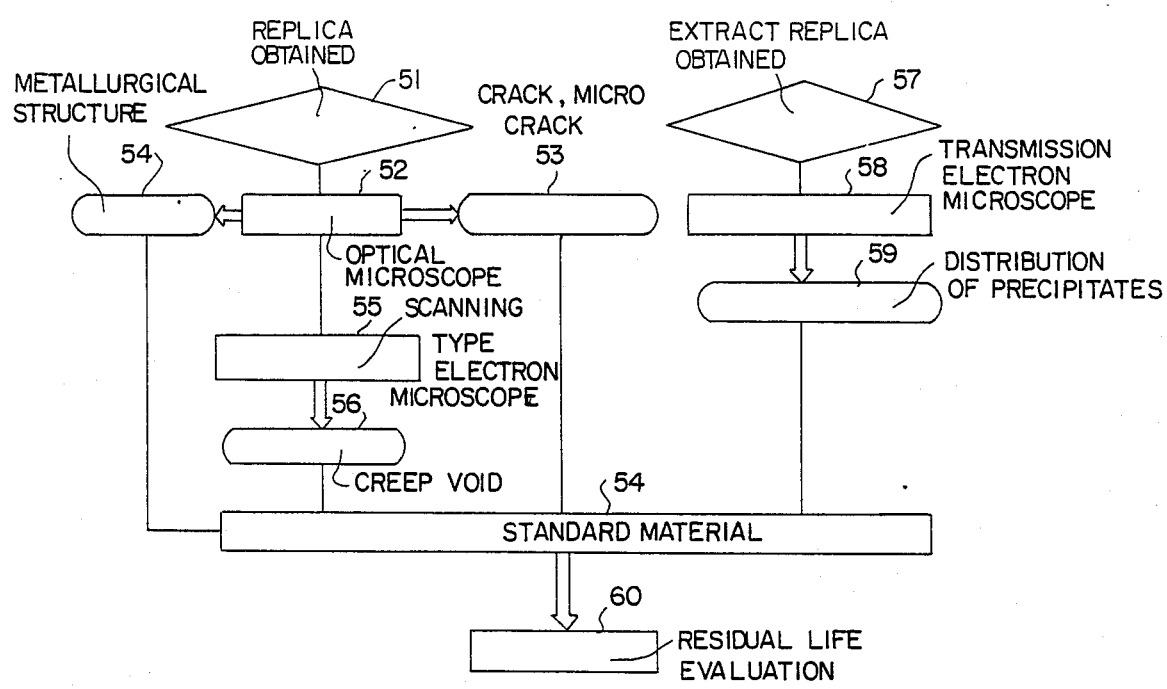
FIG. 12 is a flow chart illustrating a process in acordance with a fifth embodiment of the present invention.

A practical form of this embodiment will be described with reference to FIG. 12. A replica 51 and an extract replica 57 are obtained from the surface of a heat-resistant steel member which has been used at high temperature under a high level of stress. The replica 51 is mounted on an optical microscope for the purpose of detecting any crack and microscopic crack, as well as the state of degradation of metallurgical structure, e.g., uni-axialization of sub-grains due to re-orientation of dislocation. The result of this examination is compared with a standard structure the life consumption of which has been known through, for example, the creep rupture test, whereby the life section of this heat-resistant steel member is judged.

The factor which directly relates to the grain boundary rupture (rupture due to generation and continuation of creep voids at grain boundary) is the precipitation of $M_6C$ carbides (carbides mainly composed of Mo) and the uni-axialization of the sub-grains mentioned before. According to the method of this embodiment, the degree of change of form of the $M_6C$ precipitates is ranked through comparison with that of the standard structure.

The replica was mounted on a scanning type electronic microscope 55 for the purpose of investigation of presence and distribution of creep voids 56. The result is compared with the standard structure 54 with which the life sections are known, whereby the residual life of the tested steel is determined in terms of the life section. The extract replica 57 obtained from the same location as the replica 51 is examined by a transmission electron microscope 58 for the purpose of investigating the state of distribution of precipitates and the result is compared with that of the standard material with which the life sections have been known, whereby the residual life of the tested steel is determined in terms of the life section.

Thus, the life sections are determined through various analyses of the heat-resistant steel such as analysis of state of distribution of cracks and microscopic cracks, analysis of distribution of creep voids, analysis on the basis of change in the metallurgical structure and analysis of distribution of precipitates.

From the above life section, the residual life of the tested steel is evaluated.

Residual life evaluation test was conducted in accordance with the method of this embodiment on 2¼Cr - 1Mo steels A, B and C sampled from superheater tubes which have been used long in a boiler of a power station, the result of which is shown in the following table.

The table also shows the result of residual life evaluation conducted through a conventional method, i.e., a creep rupture test, the result of which also is shown in the same table. The factor which directly relates to the grain boundary rupture (rupture due to generation and continuation of creep voids at grain boundary) is the precipitation of $M_6C$ carbides (carbides mainly composed of Mo) and the uni-axialization of the sub-grains mentioned before. According to the method of this embodiment, the degree of change of form of the $M_6C$ precipitates is ranked through comparison with that of the standard structure.

From this table, it will be realized that the method of this embodiment makes it possible to evaluate residual life of heat-resistant steel in a short time and with a higher degree of accuracy as compared with the conventional method in a non-destructive manner.

TABLE

| Test Material (Steel) | Life Consumption (%) | |
|---|---|---|
| | Embodiment | Creep Rupture Test |
| A | 0 to 30 | 10 |
| B | 50 to 60 | 59 |
| C | 80 to 10 | 88 |

A sixth embodiment of the invention will now be described.

The present inventors have found that the kinds of precipitates in a heat-resistant steel used at high temperature and stress vary in relation to time, so that the ratio of the amount of any precipitate to the total amount of all precipitates, i.e., the relative amount, vary according to time. This means that the relative amount has a correlation to the reduction in the creep rupture life.

Thus, the sixth embodiment is to measure the relative amount of a precipitate in the sample extracted from a heat-resistant steel and to predict the residual life by locating the measured relative amount on a diagram which has been obtained before and which represents the relationship between the relative amount and life consumption.

Figure 13:
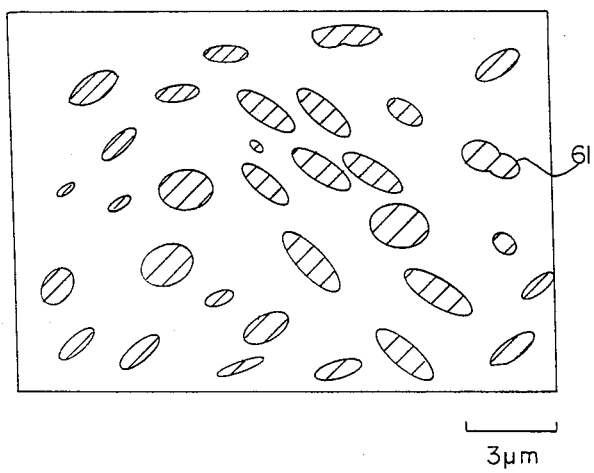

A practical example of this embodiment will be explained hereinunder with reference to FIG. 13 which is a schematic illustration of a transmission electron-microscopic structure of the extract replica which is obtained in a non-destructive manner from the surface of a pressure-resistant portion of a boiler of a power station. Using an element density quantitative analyzer attached to the transmission electron microscope, element density analysis was executed on 100 pieces of precipitates 61 on the extract replica, thus conducting identification of the precipitates, the result of which is shown in the following table.

TABLE

| Kind of precipitate | Amount of precipitation |
|---|---|
| $M_{23}C_6$ | 5% |
| $M_7C_3$ | 32% |
| $M_6C$ | 63% |

Figure 14:
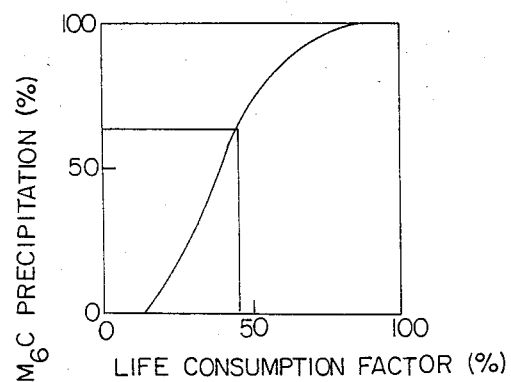

The ratio of the $M_6C$ type carbides mainly composed of Mo and Fe as the amount of precipitation of $M_6C$ was 63%. FIG. 14 shows the residual life evaluation diagram which has been beforehand obtained to show the relationship between the $M_6C$ precipitation amount and creep rupture life consumption in a heat-resistant steel which has been used for a long time to reduce its creep rupture strength. The creep rupture life consumption of the test material was predicted as being 48%, by locating the measured amount of $M_6C$ precipitation on the diagram of FIG. 14. The same pressure-resistant material was cut into pieces and subjected to a creep rupture test to measure the reduction in the creep rupture time from that of the virgin material in accordance with Larson Miller Parameter method. The creep rupture life consumption thus measured was 53% which is substantially equivalent to the value of the life consumption predicted by the method of this embodiment, whereby the effectiveness of the method of this embodiment in non-destructive prediction of residual life was confirmed.

As will be understood from the foregoing description, according to the method of the present invention, the residual life of heat-resistant steel during service at high levels of temperature and stress can be evaluated in a short time and with a high degree of accuracy in a non-destructive manner. Thus, the invention makes it possible to establish a plan of protective maintenance for improving the reliability of the apparatus in which the heat-resistant steel is used, as well as an effective non-destructive examination method.

What is claimed is:

1. A method of evaluating the residual life of a heat-resistant steel after service at high levels of temperature and stress comprising: measuring the density of an alloy element in a tiny region of each of a multiplicity of measuring spots on the surface of said heat-resistant steel; and obtaining a prediction value of said residual life by locating the data concerning the measured values of density of said alloy element on a residual life evaluation reference diagram which has been beforehand obtained and which represents the relationship between the density of said alloy element and the life consumption as obtained through a non-destructive test or a stress analysis on many pieces of said heat-resistant steel used under various conditions.

2. A method of evaluating the residual life of a heat-resistant steel having a granular structure after service at high levels of temperature and stress, comprising: obtaining a replica from the surface of said heat-resistant steel; determining the state of deterioration of the metallurgical structure of said heat-resistant steel in terms of brittle creep damage at the grain boundaries due to formation of voids and/or the state of precipitates from said replica; and obtaining a prediction value of said residual life by locating the data concerning the determined values of said state of deterioration of metallurgical structure and/or the state of precipitates on a residual life evaluation reference diagram which has been beforehand obtained and which represents the relationship between said state of deterioration of metallurgical structure and/or the state of precipitates and the life consumption as obtained through a non-destructive test or a stress analysis on many pieces of said heat-resistant steel used under various conditions.

3. The method of evaluating the residual life of a heat-resistant steel according to claim 2 wherein the evaluation employs a determination of the state of deterioration of the metallurgical structure of said heat-resistant steel.

4. The method of evaluating the residual life of a heat-resistant steel according to claim 2 wherein the evaluation employs a determination of the state of precipitates.

* * * * *